United States Patent [19]
Warren et al.

[11] Patent Number: 4,784,943
[45] Date of Patent: Nov. 15, 1988

[54] ICE NUCLEATION IMMUNOASSAY

[75] Inventors: Gareth J. Warren, San Francisco; Paul K. Wolber, Hayward, both of Calif.

[73] Assignee: Advanced Genetic Sciences, Inc., Oakland, Calif.

[21] Appl. No.: 53,126

[22] Filed: May 22, 1987

[51] Int. Cl.$^4$ ................ G01N 33/532; G01N 33/533; C12N 15/00
[52] U.S. Cl. ..................................... 435/7; 435/172.3; 435/810; 436/546; 436/800; 436/808
[58] Field of Search ................ 436/536, 56, 147, 172, 436/800, 36; 435/7, 172.3

[56] References Cited

U.S. PATENT DOCUMENTS 4,464,473  8/1984  Orser et al. ...................... 435/172.3
4,727,024  2/1988  Koocher et al. ...................... 436/36

Primary Examiner—Robert J. Warden
Assistant Examiner—Janelle Graeter
Attorney, Agent, or Firm—Clinton H. Neagley

[57] ABSTRACT

A novel method for carrying out immunoassays is described. The method involves use of a biological ice nucleating agent as a label. In particular, the method involves use of ice nucleating bacteria, or ice nucleating components derived therefrom, as a label.

35 Claims, No Drawings

ICE NUCLEATION IMMUNOASSAY

This invention relates to immunoassay methods for the detection or determination of materials in a sample. In particular, this invention relates to the use of ice nucleation agents as a label in immunoassay methods.

Immunochemical methods, and in particular immunoassays, lie at the foundation of much of present day research, medical diagnosis and environmental monitoring. Such methods utilize many technologies and methodologies but, in general, immunochemical detection techniques share three points in common. First, detection is based upon highly specific binding of a substance of interest to a receptor of biological origin. Second, the binding event is linked to a system for signal amplification and transduction into a detectable form by, e.g., visual or instrumental means. Third, there is some background signal against which the amplified and transduced signal is measured.

Immunoassays involve an immunological reaction between a ligand (e.g., antigen) in a fluid sample and a receptor (e.g., antibody) which binds specifically with the ligand. Typically one of the immunological components is conjugated with a label (an analytically indicatable group) to permit determination of the substance being assayed. Two of the more commonly used types of labels are radioisotopic labels (for radio immunoassay, or RIA) and enzyme labels (for enzyme immunoassay, or EIA). In RIA a read-out is obtained by measuring radioactivity. In EIA the read-out is obtained by measuring the catalysis of a chemical reaction in various ways, e.g., color development resulting from action of the enzyme on a color developing agent. Other types of labels or tags which have been used include fluorescent labels, chemiluminescent labels, bioluminescent labels and pH-altering labels (e.g., urease). In some immunoassays the receptor itself is the label and makes the presence of the ligand known by formation of a visible precipitate or agglutinate.

Of the various immunoassays which have been employed, two of the more common are non-competitive "sandwich" assays and competitive assays. Each of these has variations and modifications known in the art. In a typical sandwich assay, a ligand in a fluid sample is bound to an insolubilized receptor to form a ligand-receptor complex which in turn is bound to a receptor-label conjugate. The amount of label present in the resulting "sandwich" is a measure (direct) of the amount of ligand in the fluid sample. Variations of the sandwich approach include the use of suspensible or insuspensible supports; the use of onestep or two-step techniques; and the use of polyclonal, monoclonal, or double antibodies.

In a typical competitive assay, a labelled ligand is mixed with a fluid sample containing the ligand to be determined and a known amount of receptor. After mixing, the amount of label combined with the receptor is determined as a measure (inverse) of the amount of ligand in the fluid sample. Variations of the competitive approach include the use of suspensible or insuspensible supports; and the use of polyclonal, monoclonal or double antibodies.

Other types of immunoassays which have been carried out using labels include agglutination assays (e.g., involving formation of visible aggregates of microbeads) and fluorescence polarization assays (involving slowing the rate of tumbling of a fluorescent label when binding takes place).

Known immunoassay methods have been used to measure a wide variety of chemical and biological substances, including proteins (including enzymes and antibodies), polypeptides, carbohydrates, vitamins, hormones, drugs, toxins, bacteria, Rickettsiae, viruses, and parts thereof.

In general, known methods are more amenable to measuring unknown substances (unknowns) of relatively lower molecular weight. Most known methods do not lend themselves to measurements of relatively higher molecular weight unknowns present in relatively low concentration, e.g., viruses, Rickettsiae and bacteria. This is due to the fact that the binding of receptor to ligand may not appreciably affect the properties of the ligand, thereby making difficult the separation of signals from bound and unbound ligands.

Extensive general information on immunoassay techniques is available in the literature.

In a different discipline, considerable work has been done in the area of ice nucleation technology. Early studies in this area involved inorganic ice nucleating compounds, or chemical ice nuclei, such as AgI or CuS; B. Vonnegut, *Chem. Rev.*, 44, 277–289 (1949); B. J. Anderson et al., *J. Atmos. Sci.*, 33, 822–832 (1976).

More recently there have been studies of biological ice nucleating agents, also referred to herein as biological ice nuclei. It has been reported that certain bacteria, e.g., bacteria of the genera Pseudomonas (including *P. syringae* and *P. fluorescens*), Xanthomonas and Erwinia contain ice nuclei (bacterial ice nuclei) which function at temperatures just below the freezing point of water; L. R. Maki et al., *Appl. Microbiol.*, 28, 456–460 (1974); G. Vali et al., *J. Atmos. Sci.*, 33, 1565–1570 (1976); S. E. Lindow et al., *Phytopath.*, 68, 523–527 (1978); L. R. Maki et al., *J. Appl. Meteorol.*, 17, 1049–1053 (1978); S. E. Lindow, *Ann. Rev. Phytopathol*, 21, 363–384 (1983); S. E. Lindow, *Plant Dis.*, 67, 327–333 (1983). Other biological ice nuclei have been found in plants, J.O. Krog et al., *Nature*, 282, 300–301 (1979); and in insects, J. G. Duman, *Ann. Rev. Physiol*, 45, 261–270 (1983).

In studies of bacterial ice nuclei involving ultrasonic disruption of the bacteria, it has been shown that bacterial ice nuclei are concentrated in the bacterial membrane; L. R. Maki et al., *J. Appl. Meteorol.*, 17, 1049–1053 (1978). Isolation of inner and outer membrane components from *P. syringae* has demonstrated that the nuclei co-purify with the outer membranes of the Gram-negative bacteria in which they naturally occur; S. E. Lindow, *Phytopathology*, 71, 256 (1981). Examination of the frequency of ice nucleation by bacterial cells as a function of temperature has revealed a heterogenous population of nuclei; S. E. Lindow, *Plant Dis.*. 67. 327–333 (1983).

The ability to nucleate ice formation has been reported to be encoded by a single gene in several ice nucleation-positive (Ina+) bacteria, and this ability can be transferred to *E. coli* by transformation with a plasmid carrying the ice nucleation gene. C. S. Orser et al., *Molecular Genetics of the Bacterial Plant Interaction* (A. Puhler, ed.), Elsevier/North Holland Biomedical, 353–361 (1983); L. V. Corotto et al., *EMBO J.*, 5, 231–236 (1986). Sequence information for an ice nucleation gene in *P. syringae* (gene inaZ) in *P. syringae* has been reported; R. L. Green et al., *Nature*, 317, 645–648 (1985). The corresponding protein is of approximate molecular weight $1.2 \times 10^5$ Information concerning the identification and purification of this protein is reported in P. K. Wolber et al., *Proc. Nat. Acad. Sci. USA*, 83, 7256–7260, (1986). Sequence information for an ice nucleation gene in *P. fluorescens* (gene inaW) has also been reported; Warren et al., *Nuc. Acids Res.*, 14, 8047–8060 (1986).

The droplet freezing assay is a known method of testing for the presence of whole cell ice nucleating bacteria and cell-free nuclei. The method consists of laying out an array of N droplets of volume V (usually 0.01 ml) on a nucleus-free surface, cooling to temperature T (less than 0° C.) and scoring $N_f$, the number of droplets frozen. The number of nuclei/ml is then calculated by the following formula: nuclei/ml=$(1/V) \log_e [N/(N-N_f)]$. G. Vali, *J. Atmos. Sci.*, 28, 402–409 (1971).

In accordance with the invention, a method is provided for carrying out immunoassays involving immunological reactions (biospecific affinity reactions) between immunochemical counterparts wherein one of said immunochemical counterparts is linked to a label and wherein the immunoassay determination is related to or based upon measurement for the presence of label. The immunochemical counterparts (also to be referred to as reciprocal binding pair members) are ligand and receptor. The ligand and receptor are specific to, or capable of specifically binding to, each other (i.e., they exhibit specific affinity for each other). The label is a biological ice nucleating agent (biological ice nucleus), preferably a bacterial ice nucleating agent (bacterial ice nucleus). Bacterial ice nucleating agents may be used in any one or more of several forms. Bacterial ice nucleating agents may be whole cell ice nucleating bacteria, including natural bacteria and bacteria prepared by artificial, e.g., genetic engineering, methods. Bacterial ice nucleating agents may also be insoluble component parts or fragments derived from whole cell bacteria, including membranes, membrane fragments, membrane preparations and inclusion bodies. Bacterial ice nucleating agents may additionally be soluble components derived from whole cell bacteria or derived from insoluble component parts or fragments of whole cell bacteria. Such soluble components may include ice nucleating proteins (or polypeptides) and mixtures containing same. The bacterial ice nucleating agents described in this paragraph, other than whole cell ice nucleating bacteria, shall be referred to as cell-free bacterial ice nucleating agents, cell-free bacterial ice nuclei, or the like. The term bacterial ice nucleating agent shall be taken to embrace whole cell bacterial ice nucleating agents and cell-free bacterial ice nucleating agents.

The label is coupled (conjugated or linked) to one of the binding pair members in one of several ways. Coupling may involve direct covalent bonding between label and binding pair member, e.g., covalent protein-protein bonding. Coupling may also involve covalent bonding in conjunction with indirect bonding between label and binding pair member via an appropriate bridging mechanism. For instance, label and binding pair member may each be covalently bound to, respectively, biotin or avidin, thereby taking advantage of the high avidin-biotin affinity as a means to bridge label and binding pair member. Alternatively, in a preferred approach, label and binding pair member may be linked via a liposome bridge where components of the liposome are covalently bound to the binding pair member and where components of the liposome are also covalently bound to an antibody specific to the label. Coupling may also be indirect in the absence of covalent bonds, in particular, where coupling is based on immunological bridging between label and binding pair member. In a preferred method, label and binding pair member are bridged by an antibody (bridging antibody) which is specific both to the binding pair member and to another antibody which in turn is specific to the label. Protein A may also be used to link antibodies bound to ice nuclei to antibodies bound to the ligand to be detected.

Measurement for the presence of label following the immunochemical reaction may be made by any one of several ice nucleation activity assays to determine (qualitatively or quantitatively) the presence of biological ice nucleating agents. One assay is a conventional drop freezing assay. Alternatively, one may employ a novel assay method described herein. This assay (fluorescence freezing assay) comprises use of fluorescent compounds which in aqueous state manifest a change in fluorescent or visible properties upon freezing or thawing of the aqueous medium. Preferred fluorescent compounds for this method are selected from the fluorescein family, e.g., calcein and related compounds.

The method of the invention has use in a wide variety of immunoassay methods, both non-competitive and competitive, to determine (qualitatively or quantitatively) the presence of a component (analyte) in a sample. The method of the invention can be used in heterogeneous and homogeneous assays. The component being determined, i.e., one of the immunochemical counterparts, shall be referred to herein as the ligand. This component is normally an antigen, a hapten, a member of the complement system or other compound or substance to which an antibody shows binding specificity. In such instance the other one of the immunochemical counterparts (receptor) is an antibody with biospecific affinity to or for the ligand. The term antibody includes polyclonal antibodies; monoclonal antibodies; and double antibodies or anti-antibodies (i.e., antibodies specific to another antibody). Alternatively, the component to be determined (ligand) may be an antibody, in which case the corresponding receptor is a compound or substance to which the antibody is specific (e.g., an antigen, a hapten, a complement or a double antibody). The ligand is normally present in a fluid sample or, if not, is placed in aqueous solution for purposes of conducting the immunoassay.

The method of the invention has use in non-competitive immunoassays, in particular sandwich assays, as a means to determine (in particular, to quantitate) the presence of a ligand in a fluid sample. In general, such an immunoassay comprises the steps of combining or mixing a fluid sample containing the ligand to be determined with a first receptor specific for the ligand and with a conjugate comprising a second receptor specific to the ligand and a biological ice nucleating agent (label or tag) coupled to the second receptor. If the coupling of label to second receptor involves bridging groups, these groups are also considered to be part of the conjugate. The first receptor is preferably present in excess relative to the ligand and is preferably insolubilized, either in suspensible or insuspensible form, by being bound to an insoluble support. This combining results in a first complex of ligand and first receptor which in turn is reacted with the conjugate to form a second complex (sandwich) of receptor-ligand-receptor-label. The presence or amount of label bound to the ligand, i.e., bound in the second complex, is a direct measure of the presence or quantity of ligand in the fluid sample. That is, the ice nucleation activity of the second complex (sandwich) is a measure of ligand present in the sample. The receptor is normally an antibody, unless the component being assayed is an antibody (in which case, as stated, the receptor could be, e.g., an antigen or a double antibody). The first and second receptors are specific to the same ligand (i.e., the receptors are immunologically or immunochemically equivalent), but they should be capable of recognizing and binding to different, non-overlapping sites on the ligand. If the receptors are monoclonal antibodies, they should be specific to different binding sites on the ligand. A separation (e.g., washing) may be employed after the formation of the first complex. That is, the combining of the fluid sample with the first receptor may be followed by a separation which in turn is followed by a combining of the first complex with the conjugate (thus, a twostage immunoassay). A separation (e.g., washing) may also be employed after the formation of the sandwich and prior to the determination of ice nucleation activity.

Another type of non-competitive assay can be used if the ligand-conjugate complex can by itself be easily separated from unbound conjugate. In such event the ligand may be determined directly by binding to conjugate, removal of unbound conjugate and measurement of bound ice nuclei.

The method of the invention also has use in a variety of competitive immunoassays as a means to determine (in particular, to quantitate) the presence of a ligand in a fluid sample. In general, such an immunoassay comprises the steps of combining or mixing a fluid sample containing the ligand to be determined with a receptor specific for the ligand and with a conjugate comprising a biological ice nucleating agent (label or tag) and a second ligand specific for the receptor, the second ligand being coupled to the ice nucleating agent. If the coupling of label to second ligand involves bridging groups, these groups are also considered to pe part of the conjugate. The ligand to be determined and the second ligand are immunologically or immunochemically equivalent in that each is specific to the receptor. The receptor is preferably present in sufficient quantity to bind all of the ligand in the sample but not to bind all of both the ligand in the sample and the second ligand. The receptor is insolubilized, either in suspensible or insuspensible form. The above mentioned combining results in a competition for receptor. The presence or amount of label bound to the receptor is an inverse measure of the presence or quantity of ligand in the fluid sample. That is, the ice nucleation activity of the receptor-conjugate complex is a measure of ligand present in the sample. The receptor is normally an antibody, unless the component being assayed is an antibody (in which case, as stated, the receptor could be, e.g., an antigen or a double antibody). The ligand in the sample and the second ligand may be the same or essentially the same entity. A separation step (e.g., washing) may be employed prior to the determination of ice nucleation activity.

The method of the invention can additionally be used in homogeneous agglutination immunoassays where ice nuclei are immuno-bound to a complex which aggregates in the presence of the unknown. The degree of aggregation, a measure of the unknown, will be inversely related to the number of independently sorting ice nuclei measured. In a preferred form, a liposome complex is prepared which contains a liposome linked to both anti-ice nuclei antibodies and to an antibody specific to the unknown. (Alternatively, an analogous microbead complex, with microbead in place of liposome, can be used). If the complex agglutinates in the presence of the unknown, treatment of an excess of complex with, first, a known amount of ice nuclei and, second, the unknown will permit quantitation of the unknown. That is, the apparent concentration of ice nuclei (which is determined from the number of independently sorting ice nuclei) will be depressed and the unknown is determined by comparison with depression caused by known standards. This approach does not require washes or multiple sequential additions interspersed with incubations. Concentrations and incubation conditions are as found in known procedures for aggregation testing. F. J. Martin et al., *Annals N.Y. Acad. Sci.*, 446, 443–456 (1985); V. T. Kung et al., *Biochim Biophys. Acta.* 839, 105–109 (1985). This approach can be used to measure human IgM directed against denatured human IgG (human IgM is a clinical marker for human rheumatoid diseases), using liposomes bound to IgG.

The invention also comprises reagents for use in carrying out the method of the invention. In geneaal, the invention comprises a reagent for use in an immunoassay to determine the presence of a ligand in a fluid sample where such reagent is either a ligand coupled to a biological ice nucleating agent or a receptor coupled to a biological ice nucleating agent. More specifically, the invention comprises a reagent for use in a noncompetitive (e.g., sandwich) immunoassay to determine the presence of a ligand in a fluid sample, the reagent comprising a receptor specific for a ligand to be determined, said receptor being coupled to a biological ice nucleating agent. The reagent may be in solid form or in solution and may contain additional components such as pH-buffering material or stabilizers. In a preferred form the receptor is an antibody. The invention also comprises a reagent for use in a competitive immunoassay to determine the presence of a ligand in a fluid sample based upon reaction of the reagent with a receptor specific to the ligand, the reagent comprising a ligand immunologically equivalent to the ligand to be determined coupled to a biological ice nucleating agent. The reagent may be in solid form or in solution and may contain additional components such as pH-buffering material or stabilizers. In a preferred form the ligand is an antigen. The ligand to be determined may be the same or essentially the same as the immunologically equivalent ligand.

The invention further comprises kits containing reagents for carrying out the method of the invention. A kit for conducting non-competitive (e.g., sandwich) assays in accordance with the invention comprises a plurality of containers, one of which contains a receptor (first receptor) specific for a ligand to be tested, the receptor being preferably insolubilized, and a second of which contains a conjugate (as described above) comprising a receptor (second receptor) specific for the ligand to be tested coupled to a biological ice nucleating agent. A kit for conducting competitive assays in accordance with the invention comprises a plurality of containers, one of which contains a receptor specific to the ligand to be determined, the receptor being preferably insolubilized, and a second of which contains a conjugate comprising a biological ice nucleating agent coupled to a ligand immunologically equivalent to the ligand to be determined.

The method of the invention may be used to determine the presence of a wide variety of compounds or substances in solution over a broad spectrum of concentrations. The method is particularly suited for assays of relatively high molecular weight materials, e.g., $10^4$ and above, in particular, where present in relatively low concentrations e.g., $10^{-8}$ M and below.

The ice nucleation immunoassay (cryoimmunoassay) of the invention may be used in substantially any of the known immunoassays where a tag, label, detector, tracer or reporter molecule is employed. In general, except as explained otherwise herein, the method is used in accordance with known protocols and reaction conditions. Thus, conditions of temperature, time, buffer, pH, concentration, volume, molar ratios, anticontaminant additives, etc. may be employed as is known in the art, and techniques for reaction steps including mixing, washing, separating, centrifuging, etc. may be followed as is known in the art. In general, the bacterial ice nucleating agents of the invention may be sensitive to the following: temperatures above 40° C.; pH greater than 9 or less than 5; protein denaturing agents such as urea and guanidine HCl; and detergents.

The method of the invention is preferably carried out with one of the immunoreaction components insolubilized or immobilized by coupling or linking to an insoluble support. The support may be suspensible (e.g., plastic microbeads, fixed S. aureus cells, liposomes,) or insuspensible (e.g., microtitre plates, plastic tubes or beads, microtitre plates, plastic membranes, or glass surfaces), as will be understood by those skilled in the art.

Linkage to a support is created by known methods. For instance, one type of support is Polybeads available from Polyscience, Inc. 400 Valley Road, Warrington, Pa. The manufacturer provides protocols for attaching proteins to Polybeads (polystyrene beads, amino beads or carboxylated polystyrene microparticles).

Receptor antibodies (or double antibodies) may be polyclonal or monoclonal, or mixtures thereof, and are obtained through commercial sources or prepared in ways known in the art. Preferred antibody types are $IgG_1$ (e.g., rabbit, goat, or sheep polyclonal; mouse monoclonal) or $IgG_1+IgM$ (e.g., various polyclonal species).

Other standard reagents and techniques are to be employed, as will be understood in the art, including the use of analyte standards and pre-immune (blanking) sera.

A variety of types of biological ice nucleating agents (biological ice nucleating particles) may be used as a label or detector in immunoassays of the invention, with bacterial ice nucleating agents (bacterial ice nucleating particles) being the preferred type. For purposes herein, the term ice nucleation positive shall be taken to have the same meaning as ice (+) or Ina (+); the term ice nucleation negative shall be taken to have the same meaning as ice (−) or Ina (−).

Bacterial ice nucleating agents for use as labels may be whole cell ice nucleation positive bacteria, including naturally occurring bacteria and bacteria modified by genetic or biochemical means to introduce or enhance or stabilize ice nucleating properties. Preferred naturally occurring ice (+) bacteria are of the genera Pseudomonas (in particular P. syringae and P. fluorescens), Erwinia (in particular E. herbicola), and Xanthomonas (in particular X. camoestris). Bacterial strains may be isolated in known ways. A preferred approach is to (1) isolate bacteria (e.g., from above genera) as single colonies from leaves, roots, seawater, soil etc. by standard methods; (2) replica plate on nucleus-free surface with nucleus-free material (e.g., autoclaved velvet); (3) overspray with non-ice nucleating buffer mist; (4) cool to −5° C. and record position of ice (+) colonies; (5) isolate and propagate colonies; and (6) retest for ice (+) capacity.

Other whole cell bacteria may be used which have been modified genetically to introduce ice nucleation capacity using known techniques of transformation and genetic manipulation. More specifically, DNA containing an ice nucleation gene and appropriate regulatory (e.g., promoter) DNA may be introduced into a host cell via a recombinant plasmid or other vector so as to confer ice nucleating properties on the host cell.

E. coli is a preferred species for transformation in that it is well understood genetically. P. syringae is a preferred species for optimizing expression of ice nucleation activity. Preferred ice (+) DNA or ice (+) genes for introducing into bacterial strains include inaZ from P. syringae S203, R. L. Green et al., Nature, 317, 645–648 (1985); inaW from P. fluorescens MS1650, G. J. Warren et al., Nuc. Acids Res., 14, 8047–8060 (1986); and ice from P. syringae 31, C. Orser et al., J. Bact., 164, 359–366 (1985).

Various biochemically modified forms of whole cell bacteria may also be used, e.g., cells subjected to mild lysis to extract cytoplasmic material. Such lysis can be accomplished by treatment with lysozyme plus detergent (e.g., octyl thioglucoside), followed by precipitation of membranes with $MgCl_2$ (e.g., at a concentration of 40 mM). Lysis can also be accomplished by mechanical disruption, e.g., with glass beads or by sonication. Such modified whole cells are referred to as ghosts.

Whole cells will normally be used in inactivated (killed) form. For instance, coupling of the cells to receptors or ligands, e.g., with EDC, may serve to inactivate.

Preferred forms of bacterial ice nucleating agents are cellfree bacterial ice nucleating agents, in particular cell membranes or fragments thereof of any of the above described ice nucleation positive bacteria. Cell membrane fragments for use in the invention are generally of a size at or below the limit of resolution of light microscopy i.e., approximate size less than about $0.2\mu$. The sedimentation time of the fragments may be used as a measure of size (e.g., using Stoke's law). Two to twenty ice nuclei are typically recovered from each Ina (+) cell. The membranes or membrane fragments typically copurify with closed, spherical vesicles; the ice nuclei are associated with the vesicles. The cell-free nuclei are stable indefinitely if frozen at −20° C. in 10–20% sucrose; at 37° C. they are still detectable after 24 hours. Nuclei derived from Pseudomonas species nucleate at slightly higher temperatures but are less stable at room temperature as compared to nuclei derived from E. coli. Nuclei from Pseudomonas have been found to show an approximate log-linear relationship between nucleation threshold temperature and abundance from −4° to −9° C. (before coupling) and −5° to −10° C. (after coupling). E. coli-derived nuclei operate about 1° C. lower for a given nucleus concentration.

The preparation of cell-free ice nuclei from Ina (+) bacteria involves four general steps: growth of bacteria containing large numbers of ice nuclei, pretreatment of bacteria to loosen the connections between inner and outer membrane, disruption of the bacterial cells, and separation of the resulting membrane fragments from other cellular components. The methods for performing each of these tasks are well described in the literature of industrial microbiology and the literature of bacterial membrane biochemistry.

Bacteria of the genus Pseudomonas may be harvested at high levels of ice nucleus expression after growth on plates of rich, glycerol- or mannitol-containing medium, after growth at room temperature to stationary phase. Alternatively, cells may be grown in submerged culture. Cultures of E. coli expressing high levels of ce nucleation activity are obtained by growing transformed cells to mid-log phase at 37° C., then holding the culture 1 hour at 23° C. before harvest.

Pretreatments which loosen the degree of attachment of bacterial membranes to one another include plasmolysis (i.e., treatment with hypoosmotic sucrose, usually 20% w/v); incubation with 1–10 mM EDTA; treatment with 1–10 mg/ml lysozyme; and treatment with mild detergents (e.g., Triton X-100, lauryl sarkosyl, octyl thioglucoside). Bacterial cells may then be disrupted by any of several methods, including sonication, high pressure extrusion (French press), osmotic shock, and rapid depressurization.

The membrane fragments and associated ice nuclei should be separated from bacterial cytoplasmic and periplasmic components. This may be accomplished by isopycnic centrifugation in sucrose gradients, although other density-increasing solutes (e.g., Ficoll, sorbitol) may be used. Alternatively, other methods of separation may be used, including electrophoresis and filtration.

The above manipulations are best accomplished at 0° to 4° C. and at a pH between 6 and 8.5. A preferred buffer is 30 mM tris, pH 8.0. All reagents and labware should be protease-free. Protease inhibitors (such as phenylmethylsulfonylfluoride and leupeptin) may be included during the loosening and disruption steps.

Another preferred form of ice nucleating agent is a solution of detergent-solubilized ice nuclei. In general, such nuclei are smaller than their membrane counterparts, and nucleate at lower temperatures than membrane-bound ice nuclei. Detergent solubilized ice nuclei are stable for a few days at room temperature; they are, however, less stable than membrane-bound ice nuclei.

Soluble ice nuclei may be prepared either by extraction of membrane-bound ice nuclei, e.g., with 40 mM octyl thioglucoside or by extraction of ice nucleating inclusion bodies with a mixture of 40 mM octyl thioglucoside and 2 M urea. Solubilized ice nuclei are then separated from insoluble nuclei by ultracentrifugation.

Cell-free bacterial ice nucleating agents may also be obtained as ice nuclei extracted from the cytoplasm of ice nucleation positive bacteria, in particular bacteria genetically modified for over-production of ice nuclei (e.g., by introduction of efficient promoter systems or by introduction of multiple copies of ice (+) DNA).

Other forms of cell-free bacterial ice nucleating agent include synthetic counterparts of membrane fragments or membrane ice nuclei, e.g., ice (+) proteins isolated from ice (+) strains and reconstituted with lipids.

Biological ice nucleating agents may be linked to one of the immunochemical counterparts (receptor or ligand) for use as a label (biological ice nucleation label or bacterial ice nucleation label) in the immunoassays of the invention (the linked unit referred to as the conjugate) in any one of several ways.

Linkage may be by covalent protein—protein bonding between label and receptor or ligand using techniques known in the art with, as stated, a preferred label being a membrane fragment, or fragment thereof, from an ice nucleation positive bacterial strain. Preferred covalent linking agents (linking means) include glutaraldehyde, succinimides, and maleimides. Cross linking reagents and preparation protocols for various ways to link are available from Pierce Chemical Company, Rockford, Ill. 61105; preferred among these are succinimidyl-4-(p-maleimidophenyl) butyrate and N-succinimdyl-3-(2-pyridyldithio)propionate, and ethyl(-dimethyl aminopropyl)carbodiimide (EDC). EDC functions by activating carboxylate groups and causing them to reach to form covalent bonds with amine, phenol and alcohol groups.

Linkage may also be accomplished using the known strepavidinor avidin-biotin system. For instance, the biological ice nucleation agent (the label) can be conjugated (by covalent bond) to biotin and the resulting biotin-label complex coupled to a ligand-biotin (covalent) complex or a receptor-biotin (covalent) complex via an avidin bridge, thereby serving to link the ligand or the receptor to the label. Alternatively, the label can be conjugated to avidin or strepavidin and the resultant complex coupled to a ligand-biotin complex or a receptor-biotin complex, thereby serving to link the ligand or the receptor to the label. See, in general, D. A. Fuccillo, *Bio-Techniques*, 3, 494–501 (1985) and E. A. Bayer et al., *Methods of Biochemical Analysis*, 26, 1–45 (1980) regarding avidin-biotin complexes.

Another basis of binding pair member-label linkage is indirect liposome bridging. There are known methods for covalently bonding liposomes to proteins, e.g., antibodies. F. J. Martin et al., *Annals of N.Y. Acad. of Sci.*, 446, 443–456 (1985); V. T. Kung et al., *Biochim. Biophys. Acta*, 839, 105–109 (1985); F. J. Martin et al., *Biochem.*, 20, 4229 et seq. (1981); F. J. Martin et al., *J. Biol. Chem.*, 257, 286 et seq. (1982); L. D. Leserman et al, *Nature*, 288, 602 et seq. (1980). By covalently bonding a liposome both to a binding pair member and to an antibody specific to the label, the liposome can serve as a bridge between binding pair member and label, i.e., pair member-liposome-antibody-label.

Linkage to label in the absence of covalent bonding can also be created using immunological bonding. Thus, an antibody specific to both label and bonding pair member can serve as a bridge. Alternatively, one can use as a bridge an antibody specific to both label and a second antibody, where the second antibody is specific to the bonding pair member.

As will be appreciated by those in the art, various bridging combinations using antibodies, double antibodies, bifunctional antibodies, liposomes, avidin-biotin complexes, protein A (which binds antibodies), protein G (which also binds antibodies) or the like can be employed to bind label to binding pair member, with the understanding that binding constants and stability of the bridge components must be such as to allow the bridge to remain intact for purposes of the immunoassay.

For use of the invention with immunoassays involving binding of ice nuclei to a solid phase (i.e., heterogeneous assays), in particular if the solid phase is in a form other than finely divided particles, it is preferable to release the ice nuclei from the solid phase prior to determining the number of ice nuclei present. This follows from the fact that ice nuclei are most easily assayed as independently sorting particles. Release of nuclei may be brought about in ways known in the art.

Where ice nuclei are bound to a solid support via an antibody which in turn is linked to the support by a disulfide bond, a preferred method of release is treatment with dithothreitol (DTT). Such treatment, e.g., 30 minutes at room temperature with 20 mM DTT in 20 mM Tris at pH 8.0, results in release of the antibody together with an ice nuclei bound to the antibody. This method of release can be used where ice nuclei are linked to a binding pair member by a lipsome bridge or by immunological bonding, as described above.

Other release agents which may be used are proteolytic enzymes. For instance, some forms of bacterial ice nuclei are resistant to papain and trypsin, and these enzymes can be used to free (meaning, to release) bound nuclei where the nuclei are bound to the support via an antibody (that is, where at least one link between ligand and label is an antibody, whether or not that link involves covalent bonds).

Papain cuts antibodies in the hinge region of the immunoglobulin, separating the combining sites from one another and destroying immunobridging. Illustrative conditions for treatment with papain are as follows: treatment with 100 μg/ml papain in pH 7 buffered solution containing 10 mM B-mercaptoethanol, 2 mM EDTA at room temperature for 30 minutes; reaction can be stopped by addition of an inhibitor (e.g., $H_2O_2$) or by chilling and diluting.

Trypsin works at neutral pH and can be inactivated with a specific inhibitor (soybean trypsin inhibitor). Illustrative conditions for treatment with trypsin are as follows: treatment with 50 μg/ml trypsin in 10 mM $NaP_i$ pH 7.0 buffer at room temperature for one hour; reaction can be stopped by cooling on ice.

In general, for each form of immunoassay there are immunological reactions which either go to completion or reach an equilibrium. For instance, in the sandwich assay the reactions result in a sandwich complex which is measured as an assay for the unknown. In competitive assays the reactions result in system containing one or more products which can be measured as an assay for the unknown. In the immunoassays of the invention, the presence of the analyte in the original fluid sample is determined or quantitated by determining, after completion of the immunological reactions, the presence or amount of reaction product containing label. Specifically, this is done by selectively measuring the ice nucleation activity of such reaction product, and correlating the level of activity with the presence of ligand in the sample. That is, the presence of ice nucleating agent in an immunological reaction product is related to and indicative of the presence of analyte in the sample.

The presence or amount of label may be determined by any form of ice nucleation assay. A known type of assay is the droplet freezing assay in which the concentration of ice nuclei is measured by serially diluting a suspension of the nucleator in nucleus-free buffer, and then scoring (e.g., by visual observation) the number of nucleation events (droplets frozen, $N_f$) when an array of N droplets of volume V (e.g., 10 μl droplets, 30–50 per dilution) is laid out on a nucleus-free surface (e.g., a paraffin-coated aluminum foil boat) and cooled to the chosen temperature T (less than 0° C.). Nucleus-free buffer may be prepared by autoclaving aliquots (e.g., 10 ml) of a buffer in clean culture tubes, chilling the tubes to −10° C., and discarding any tubes that freeze. The number of nuclei/ml at each temperature is calculated via a standard formula from Poisson statistics:

$$C = DV^{-1} \ln(N_T/N_U)$$

where C is nuclei/ml; D is the dilution factor (e.g., for a 1 to 100 dilution, D is 100); V is the drop volume in ml; $N_T$ is the total number of drops tested; and $N_U$ is the number of unfrozen drops (i.e., N minus the number of frozen drops). In general, solutions of assay standards and unknowns are prepared, C is measured, a standard curve of C versus standards is constructed, and amounts of unknowns are calculated. If 40 drops of volume 0.01 ml, diluted 1:1000 from the original sample, are tested at −5° C., and 30 drops freeze, then the concentration of nuclei at −5° C. is $(1000/0.01) \ln(40/10) = 1.4 \times 10^5$/ml. See G. Vali, *J. Atmos. Sci.*, 28, 402–409 (1971) regarding the droplet freezing assay. The Vali procedure, as particularized above, will be referred to in the Examples below as the Vali procedure.

The scoring of nucleation (freezing) events in the droplet freezing assay may also be done in ways other than visual observation of ice formation. Any physical change which occurs upon freezing can be the basis for determining whether freezing has occurred. Thus, release of heat (calorimetry) can be measured. Also, depolarization of light by scattering can be measured. A preferred approach, which lends itself to automation, is measuring the change in conductivity upon freezing. This approach is based upon the fact that freezing results in the immobilization of current-carrying ions present in water. The result is a precipitous drop in conductivity upon freezing.

A preferred method of detecting the freezing of droplets in ice nucleation assays, referred to herein as a fluorescence freezing assay, involves use of concentration-dependent, fluorescence quenching dyes ("fluorescence quenching dyes"). Such assays are conducted by observation of the quenching of fluorescence of a fluorescent dye, e.g., calcein (a fluorescein derivative), which takes place as the droplet freezes. More specifically, such an assay may be carried out as follows. Calcein (absorbance maximum 490 nm; emission maximum 520 nm) is included in the nucleus-free buffer in which the test is to be performed, at a concentration of 1 mM. The test area is illuminated with near-UV radiation (300 nm to 400 nm), which causes the droplets to fluoresce green. As a droplet freezes, its fluorescence diminishes, then is extinguished. This change is easily observed, either by a human operator or an automated instrument. Other dyes which may be used include other members of the fluorescein family (e.g., eosin) and rhodamine. Donoracceptor pairs as described below may also be used.

The method operates via the principle of concentration-dependent fluorescence quenching. With reference to calcein, the principle may be explained as follows. As water in the droplet freezes, calcein (which is highly water-soluble) is concentrated in the remaining unfrozen water. This decreases the average distance between dye molecules, causing them to exchange excitation energy by nonradiative ("Forster") energy transfer. This process depends upon the inverse sixth power of the distance between molecules, and upon the degree of overlap between the absorbance and emission spectra. At some point, the excitation energy hops among so many molecules that it is likely to encounter a trap (a molecule which can easily degrade the excitation into heat, without emission of light). At this point the fluorescence fades; as the dye grows more concentrated, the traps overwhelm the tendency of individual molecules to fluoresce, until all fluorescence is quenched.

Fluorescein and its derivatives are particularly well suited to this test, in that they are highly water soluble, highly fluorescent, show a good degree of overlap between absorbance and emission spectra, and naturally contain some molecules capable of acting as traps. It should be noted, however, that other dyes (such as the rhodamines) show some degree of concentration-dependent fluorescence self-quenching. In addition, any highly water-soluble dye can be used in this test if a suitable concentration of a nonfluorescent trap molecule (here called an acceptor) is included in the solution. A suitable acceptor should be highly water-soluble, nonfluorescent, and should absorb strongly at the emmission maximum of the fluorescent dye (here called the donor).

For calcein, fluorescence self-quenching begins at about 10 mM, and is complete at 60 mM. The initial concentration is chosen low enough that the calcein does not depress the freezing point of the test buffer, but high enough that quenching will be significant before the droplet is completely frozen. In practice, 1 mM is a good working concentration for calcein.

The standard ice nucleation assay may be automated by observing the test with a suitable detector, such as a video camera or photodiode array, and coupling the output of the detector to a microcomputer programmed to note the bath temperature at which the fluorescence of a given drop fades below some threshold fraction of its initial intensity. Alternatively, droplets may be dispersed in a silicone oil, F. Franks et al., *Cryobiology.* 20, 298–309 (1983), which effectively isolates them from one another. The total fluorescence can then be monitored as a function of temperature; the ratio $F_i/F(T)$ is the same as the ratio $N_T/N_U$ in a conventional nucleation assay. In the above ratio, $F_i$ is the initial fluorescence (no frozen droplets), and $F(T)$ is the fluorescence at temperature T, where some drops in the dispersion have frozen.

The immunoassays of the invention can be carried out to test for a wide variety of analytes, both of clinical interest (e.g., serum antibodies or other components), environmental interest (e.g., toxins) and otherwise, over a broad range of molecular weights. Lower molecular weight analytes such as drugs, hormones and toxins can be assayed (e.g., digoxin, thyroxins, and cocaine). Higher molecular weight analytes can also be measured such as antibodies and other proteins (e.g., human anti-HIV antibody, human alpha-fetoprotein and hepatitis B surface antigen). The method of the invention may also be employed for analytes of very high molecular weight such as bacteria and viruses (e.g., human immunodeficiency (AIDS) virus and hepatitis B virus).

The method of the invention provides a rapid means of conducting immunoassays with high sensitivity and low background. This is a consequence of the nature of the approach whereby the binding of one nucleus is amplified by the freezing of an entire drop of water. Because it is possible to distinguish whether a 10 $\mu$l drop of water contains zero or one ice nucleating agent, the agent is capable of detecting a single binding event in an immunoassay. The sensitivity varies over at least four orders of magnitude as the temperature decreases from $-5°$ C. to $-10°$ C. Thus, the dynamic range is large and the gain is adjustable by changing the measurement temperature. Ice nuclei can be measured at levels as low as one per 100 $\mu$l of liquid. At one ice nucleus per molecule of ligand, this would correspond to a ligand concentration of $1.7 \times 10^{-20}$ M. The assay can be used for large (greater than $10^7$ daltons), biologically active particles such as viruses and bacteria over an approximate range of $10^{-20}$ to $10^{-7}$ M (concentrations as low as $10^{-20}$ M are clinically significant). Such particles are highly multivalent, so that at $10^{-20}$ M the effective concentration of ligand is greater than $10^{-17}$ M. For more conventional ligands ($10^3$-$10^6$ daltons), the assay can be used over an approximate range of $10^{-12}$ M to $10^{-7}$ M (this range is clinically significant).

For tests at low dilution (i.e., maximum sensitivity for detecting very low concentrations of analyte), care should be taken to minimize background (non-specific) binding of nuclei and to assure that the immunological affinity is sufficiently high.

With the fluorescence freezing assay, if the drop has a volume of 10 $\mu$l and contains 1 mM fluorescein one binding event can turn off the fluorescence of $6 \times 10^{15}$ molecules of fluorescein. If replicate drops are tested, the primary source of error will be counting (Poisson) noise, which means that the statistical significance of high sensitivity tests will be well characterized and calculable.

For biological ligands, e.g., bacteria or viruses, the sensitivity of the ice nucleation immunoassay means that prior biological amplification is not necessary. For instance, bacterial blood infections are usually diagnosed by culture of blood on a suitable medium. A bacterial concentration of $10^6/l$ ($1/\mu l$) is relatively high; concentrations of $10^4/l$ may cause significant clinical effects. Thus, culture of 100 $\mu$l of blood on a petri plate might produce only one or a few colonies; each colony would represent, approximately, a $10^7$ amplification (by bacterial growth), but the assay would require a clinically critical 18–24 hour growth period. The ability to detect low blood concentrations of bacteria directly (or after shorter growth period) in accordance with the invention constitutes an advance of clinical significance.

In general, background in the form of non-label ice nuclei will not be a major problem for the method of the invention. Most liquids of biological origin (e.g., serum, urine) are devoid of ice nuclei at $-5°$ C. and contain only low concentrations of nuclei at $-10°$ C. The main source of background nucleation in the cryoimmunoassay is nonspecific binding of labels to the assay complex. This applies to immunoassays in general and established strategies for dealing with nonspecific binding are known in the field.

An important feature of the method is that the gain is variable by varying the assay temperature. This is due to the fact that the abundance of nuclei increases smoothly over several orders of magnitude between some threshold temperature (e.g., $-5°$ C. for cell-free membrane fragments) and some plateau temperature (e.g., $-12°$ C.). Tests may be optimized by assaying a series of dilutions over a range of temperatures and selecting the combination of dilution and temperature which provides the best signal to noise ratio for the given analyte.

Other advantages of the invention include the small sample size that can be used and the avoidance of need for hazardous reagents or expensive equipment. In addition, freezing provides a stable signal so that timing of the reading is not critical.

EXAMPLES

Abbreviations used in the Examples below include the following:

(a) Proteins

AFP alpha-fetoprotein
AP alkaline phosphatase
ProA Protein A (b) Antiboides

GaRIG goat anti-(rabbit immunoglobulin)
MaAFP mouse anti-(AFP)
RaECM rabbit anti-(E. coli membrane)
RaINA rabbit anti-(InaW protein, denatured)
Of the above, MaAFP is monoclonal, other are polyclonal.

(c) Other

| (a) Proteins | |
|---|---|
| AFP | alpha-fetoprotein |
| AP | alkaline phosphatase |
| ProA | Protein A |
| (b) Antibodies | |
| GaRIG | goat anti-(rabbit immunoglobulin) |
| MaAFP | mouse anti-(AFP) |
| RaECM | rabbit anti-(E. coli membrane) |
| RaINA | rabbit anti-(InaW protein, denatured) |
| Of the above, MaAFP is monoclonal, others are polyclonal. | |
| (c) Other | |
| L | liposomes |
| m* | cell-free ice nuclei produced from membranes of E. coli transformed by an Ina gene. |
| s* | soluble cell-free ice nuclei |

Operators used in the Examples to denote immune reactions are as follows:

() Parentheses, used to produce unambiguous schemes; evaluate reactions inside parentheses first.
:: Covalent linkage.
→ Receptor-ligand reaction, with the reagent on the right added to that on the left.
← Receptor-ligand reaction, with the reagent on left added to that on the right.

EXAMPLE 1 PREPARATION OF ICE NUCLEI (a) Bacterial Strains and Culture Conditions.

The host used for all plasmids was E. coli K12 strain JC10291; D. K. Willis, et al., Mol. Gen. Genet., 183, 497–504 (1981); ara galK his lacY leuB mol proA rpsL suoE thi thr tsx (recA-srl)303. For ice nucleation, protein, and membrane studies, E. coli were cultured with aeration at 37° C. in Luria broth (10 g tryptone (Difco), 5 g yeast extract (Difco), 5 g NaCl, and 1 g glucose, per liter) containing 100 μg/ml ampicillin and 250 μM isopropyl-B-D-thiogalactopyranoside, to an $OD_{600}$ between 0.4 and 0.5. Cells were then grown for an additional hour at 23° C. (final $OD_{600}$ less than 0.8), chilled 15 min on ice, and harvested by centrifugation.

(b) Construction of pMWS10.

The region of DNA encoding the P syringae S203 inaZ gene; R. L. Green, et al., Nature, 317, 645–648 (1985); was digested with restriction enzymes AhalII (cutting at nucleotide 775) and EcoRl (cutting at nucleotide 4453), resulting in a fragment beginning 23 base pairs 5' to the initiator codon. The EcoRl end was converted to a HindlII end by addition of a linker, and the fragment was inserted into pKK223.3; J. Brosius, et al., Proc. Nat. Acad. Sci. U.S.A. 81, 6929–6933 (1984); so that inaZ was placed downstream of the tac promoter. The construct retained the original ribosome binding site of inaZ. The plasmid pMWS10 was then used to transform E. coli to the Ina (+) and ampicillin resistant phenotypes.

c. Bacterial Membrane Preparations (m*).

Inner and outer membrane fractions were prepared from E. coli harboring pMWS10 by the method of K. Ito, et al., Cell, 11, 551–559 (1977), as described, except that 1 mM phenylmethylsulfonylfluoride (PMSF) was included during lysozyme treatment, and sonication was performed in the presence of 10 mM EDTA.

Harvested cells were washed once with ice-cold 30 mM Tris, pH 8.1 (10% of culture volume), and pelleted by centrifuging at 5000 rpm, for 5 min., in an SS-34 rotor. All subsequent manipulations were performed on ice. The cells were resuspended in 20% w/v sucrose, 30 mM Tris, pH 8.1 (1% of culture volume). To this was added 100 mM PMSF in 2-propanol (0.01% culture volume), 2.5 mM leupeptin (0.005% culture volume), and 1 mg/ml lysozyme in 0.1 M EDTA, pH 7.5 (0.1% of culture volume; stock freshly made). Cells were incubated motionless, on ice, for 30 min.

The cells were then centrifuged at 11,500 rpm for 15 min., in an SS-34 rotor. The supernatant was removed, and the pellet resuspended in 20% w/v sucrose, 10 mM EDTA, pH 7.5 (1% of culture volume). Again, leupeptin (0.005% of culture volume) was added. The suspension was then sonicated with a tip sonicator at 100W. Sonication was performed on ice, using 15 sec. bursts, with 1 min. rests between bursts, until the suspension clarified markedly, and there was no evidence of unsheared DNA (suspension no longer slimy).

The suspension was diluted with an equal volume 10 mM EDTA, and centrifuged at 4000 rpm for 10 min. (SS-34) to remove unbroken cells. The supernatant was loaded over 15% w/v sucrose, 5 mM EDTA (pH 7.5). A 1 ml cushion of 70% w/v sucrose, 5 mM EDTA, was included at the bottom of the tube. The tube was ultracentrifuged for 1 hr. at 50,000 rpm in a Beckman SW-50.1 rotor. Membranes were recovered from the 15%/70% interface, while a dense fraction (inclusion bodies) was recovered from the bottom of the 70% sucrose cushion.

The harvested membranes were diluted 1:1 with 5 mM EDTA, pH 7.5 and layered onto step gradient consisting of 53% w/v sucrose, 5 mM EDTA over a 70% w/v sucrose, 5mM EDTA cushion. Samples were ultracentrifuged overnight, 50,000 rpm, in the SW50.1 rotor. Inner membrane (with comigrating ice nuclei) was recovered from the top of the 53% sucrose layer, while outer membrane was recovered from the 53%/70% interface.

d. Preparation of Solubilized Bacterial Ice Nuclei (s*).

The dense fraction (inclusion bodies) from cells harboring pMWS10 was extracted with 40 mM octylthioglucoside (OSG, from Calbiochem-Behring). The solubilizer (80 mM OSG, 10 mM Tris (pH 7.8), 0.7 M sucrose, 13 mM dithiothreitol, DTT) was mixed 1/1 (v/v) with the total membrane suspension (ca. 5 mg protein/ml), incubated for 30 min at 37° C., then ultracentrifuged 1.5.hr at 4° C., 215,000xg, to remove undissolved material. The insoluble material was then treated for 1 hr at 37° C. with OSG solubilizer containing 2M urea, and here the supernatant was retained after ultracentrifugation. The supernatant contained approximately 10% of the total InaZ protein present in the original dense cell fraction, and was active in ice nucleation after 1:100 dilution into 10 mM KPi buffer (pH 7.0, 4° C.). Finally, the supernatant was passed over a sephacryl S-400 column, eluting with a buffer containing 2 M urea, 100 mM NaP$_i$(pH 6.4), 12 mM OSG, and 1 mM DTT, at 6.0 ml/hr and 4° C. The most active fractions, which eluted near the void volume of the column, were pooled, flash-frozen, and stored at −20° C. until use.

EXAMPLE 2

Immunosorption and Immunorecognition Using Fixed S. aureus and Ina(+) Membrane Preparations Inner and outer bacterial membrane preparations were prepared, harvested, purified and recovered as in Example 1. The inner and outer membranes were pooled (referred to below as the cell-free nuclei). The cell-free nuclei were incubated with either RaECM antiserum or rabbit preserum (control). RaECM was prepared in the same way as the preparation of RaINA described in Example 3, except (1) the material used to elicit antibody production consisted of pooled inner and outer membranes prepared as in Example 1 starting from Ina (−) *E. coli* JC10291, D. K. Willis, et al., *Mol. Gen. Genet.*, 183, 497–504 (1981), into which plasmid pACYC184, A. C. Y. Chang et al., *J. Bacteriology*, 134, 1141–1146 (1978), was introduced using standard techniques; and (2) 1 mg doses were used for the initial and booster inoculations.

Conditions for incubation were room temperature for 2.5 hr, as follows:
- 100 μl antiserum or preserum
- 100 μl 100 mM EDTA, pH 7.5
- 5 μl cell-free ice nuclei (m*)
- 795 μl 1% w/v gelatin (Bio-Rad) in TBS. Tris-buffered saline (TBS) contains 20 mM tris and 150 mM NaCl (pH 7.5). At the same time, formalin-fixed (Sigma) *S. aureus* cells (which bear Protein A on their surface) were incubated with GaRIG (Sigma R-3128), IgG fraction, 12.6 mg protein/ml, as follows:
- 20 μl *S. aureus* cell suspension
- 100 μl GaRIG
- 100 μl 100 mM EDTA, pH 7.5
- 780 μl 3% w/v gelatin in TBS.

After incubation, the fixed *S. aureus* cells were microfuged 3 min. (Beckman microfuge, 2000 rpm), and the pellet washed once with 1 ml 1% gelatin in TBS. The pelleted cells were again resuspended in 1% gelatin/TBS, divided between two 1.5 ml plastic Eppendorf tubes, microfuged, and the supernatants discarded. The pellets were resuspended in the entire contents of either the antiserum or preserum/nucleus mixtures, incubated 1 hr. at room temperature, then 30 min. at room temperature on a rotating wheel mixer. The pellets were each washed with 3×1 ml of TBS (2000 rpm, 3 min.), resuspended in 1 ml ice nucleus-free 10 mM NaP$_i$ buffer (0° C.), incubated on ice 30 min., and tested for ice nucleation via droplet freezing assay in accordance with the Vali procedure (see description of same above). The results of this experiment, shown in Table I below, demonstrate a ca. 20x excess of nuclei absorbed by cells when the ice nuclei are pretreated with RaECM. In Table I, temperature is degrees C; S is sample; C is control; units in the second and third columns are ice nuclei/ml. The linkage involved may be represented as:

Fixed *S. aureus*::ProA→GaRIG→(RaECM→m*)

TABLE I

| Temperature | RaECM (S) | Pre-RaECM (C) | S/C |
|---|---|---|---|
| −6.0 | $1.39 \times 10^2$ | $1.05 \times 10^1$ | 13.2 |
| −6.5 | $9.16 \times 10^2$ | $5.11 \times 10^1$ | 17.9 |
| −6.9 | $5.98 \times 10^3$ | $1.05 \times 10^2$ | 57.0 |
| −7.5 | $1.62 \times 10^4$ | $2.88 \times 10^2$ | 56.3 |
| −8.2 | $7.99 \times 10^5$ | $9.16 \times 10^3$ | 87.2 |
| −9.1 | $3.57 \times 10^6$ | $1.72 \times 10^5$ | 20.8 |
| −10.3 | $2.68 \times 10^7$ | $6.93 \times 10^5$ | 38.7 |
| −12.4 | $3.25 \times 10^7$ | $9.99 \times 10^5$ | 32.5 |

The results demonstrate that membrane-bound ice nuclei can be used to detect immunorecognition events.

EXAMPLE 3

Immunosorption and Immunorecognition Using Microbeads and Soluble Ice Nuclei (s*)

(a) Preparation of RaINA

InaW protein was obtained from *E. coli* LC41 prepared in accordance with the description provided in L. V. Corotto et al., *EMBO J.*, 231–236 (1986). Samples of the InaW protein were prepared by electroelution, M. W. Hunkapiller et al., *Methods Enzymol.*, 91 227–236 (1983), from a preparative SDS-polyacrylamide gel (first immunization), enrichment of total bacterial membranes for the InaW protein by OSG extraction (first booster) as described in P. K. Wolber et al., *Proc. Natl. Acad. Sci. U.S.A.*, 83, 7256–7260 (1986), or complete purification (all subsequent boosters) of the InaW protein as reported in P. K. Wolber et al., *Proc. Natl. Acad. Sci. U.S.A.*, 83, 7256–7260 (1986). Purified protein aliquots were dialysed against 1 liter sterile 50 mM (NH$_4$)HCO$_3$ buffer (pH 7.0), with 4 changes over 20 hours in the cold, concentrated in a vacuum-centrifuge (Savant), brought to the desired volume with sterile phosphate buffered saline (PBS: 10 mM NaP$_i$, 150 mM NaCl), pH 7.0, and stored frozen at −20° C. until use.

Polyclonal antibody production was performed by Berkeley Antibody Company, Inc. (Richmond, Calif.). The rabbit initially received a peri-lymph nodal injection of 500 μg of antigen emulsified with Freund's Complete Adjuvant. The rabbit was given boosters of approximately 250 μg antigen in Freund's Incomplete Adjuvant every three weeks and bled ten days after each boost.

An IgG rich fraction of the antiserum was obtained by 40% ammonium sulfate precipitation of the antiserum; W. B. Dandliker et al., *Methods in Enzymol.*, 74, 3–28 (1981). The final pellet was resuspended in ½ the original volume PBS and dialyzed against PBS containing 0.01% thimerosal.

b. Immunosorpotion and Immunorecognition

RaINA was immunosorbed by GaRIG covalently linked to polyacrylamide microbeads (GaRIG-microbeads obtained from Immunobeads, Bio-Rad Labs). Immunobeads exposed to an incubation mixture, in which TBS was substituted for RaINA, were used as control. The immunosorption incubation mixture was:
- 100 μl RaINA serum or TBS
- 200 μl Immunobeads in PBS/0.1% w/v BSA
- 700 μl TBS, where PBS (phosphate-buffered saline) is 10 mM NaP$_i$, 154 mM NaCl, pH 7.5, and BSA is bovine serum albumin, radioimmunoassay grade (Sigma).

The experimental and control mixtures were incubated on an Adams nutator, at room temperature, for one hour, then spun out with a Beckman microfuge, 2000 rpm for 10 min. The supernatants were discarded, and the pellets washed with 1 ml TBS. The pellets were then resuspended in 990 µl TBS.

Solubilized bacterial ice nuclei (s*) were prepared and purified as in Example 1. 10 µl of s* solution was added to the pellets resuspended in 990 µl TBS. The mixture was incubated on the nutator, at room temperature, for 4 hr. The beads were again centrifuged out, the supernatants discarded, and the pellets washed with 2×1 ml TBS. The pellets were resuspended in 1 ml each Ina(−) 10 mM NaP$_i$ solution, incubated on ice for 30 min., and tested for ice nuclei via the droplet freezing assay in accordance with the Vali procedure (see description of same above).

The results of this experiment, shown in Table II below, demonstrate a ca. 15× excess of nuclei absorbed by the experimental beads. In Table II, temperature is degrees C; S is sample; C is control; units in the second and third columns are ice nuclei/ml. The linkage involved may be represented as:

Microbead::GaRIG→RaINA→s*

TABLE II

| Temperature | RaINA (S) | No Antibody (C) | S/C |
|---|---|---|---|
| −8.9 | $6.93 \times 10^3$ | 0.0 | Infinity |
| −9.4 | $5.98 \times 10^4$ | $4.31 \times 10^3$ | 13.9 |
| −10.1 | $2.39 \times 10^5$ | $1.39 \times 10^4$ | 17.2 |
| −11.3 | $9.16 \times 10^5$ | $6.93 \times 10^4$ | 13.2 |

The results demonstrate that soluble ice nuclei can be used to detect immunorecognition events. The experiment also shows that nuclei can be immunosorbed via a specific antibody under conditions where the nuclei themselves are not pelleted in a microfuge. The experimen further demonstrates an immunoassay for a ligand (RaINA) under non-competitive conditions wherein the ligand undergoes immunological reaction with a receptor (GaRIG) and wherein detection involves a bacterial ice nucleating agent. In addition, the experiment shows temperature-dependent sensitivity, i.e., the number of nuclei detected is temperature dependent. The number of nuclei increases as temperature increases resulting in a greater signal at increased temperature.

EXAMPLE 4

Noncompetitive Sandwich Assay for AFP Using Bridging Liposomes

Alpha-fetoprotein (AFP) is assayed in a noncompetitive sandwich assay using soluble bacterial ice nucleating agents bound to the unknown by a bridging liposome complex as described below.

(a) Preparation of Bridging Liposome

A bridging liposome complex comprising liposome covalently bound both to rabbit polyclonal antibodies against AFP (RaAFP) and to rabbit polyclonal antibodies against the soluble ice nucleating agents of Example 1 (RaINA) is prepared. RaAFP is obtained commercially (CalBiochem, La Jolla, Calif.). RaINA is prepared as in Example 2. The two antibodies are derivatized by reaction with N-succinimdyl-3-(2-dithiopyridyl)-propionate; F. J. Martin et al., Biochem., 20, 4229 et seq. (1981).

The two derivatized antibodies are mixed at 1–10 mg protein/ml and then activated by mild reduction with dithiothreitol (DTT) at pH 4.5 to cleave away the 2-thiopyridyl group leaving a free sulfhydryl group. The activated antibodies are bound to the same liposome by mixing with liposomes doped with ca. 5 mole percent of 3-(2-dithiopyridyl)propionylphosphatidylethanolamine. The mixture is reacted overnight and unreacted antibodies are separated from the bridging liposome complex by column chromatography (Biogel P-200) or pelleting in an ultracentrifuge. The result is a liposome to which RaAFP and RaINA are linked via easily cleaved disulfide bonds (i.e., bound nuclei may be released by treatment with DTT as described below).

The above procedures for preparation of liposome binding complex bound to antibodies are carried out in accordance with F. J. Martin et al., Biochem., 20, 4229 et seq. (1981).

(b) Preparation of Bridging Liposome Complex Bound to Ice Nucleating Agent

Soluble ice nucleating agent is prepared as in Example 1. This is bound to the bridging liposome complex prepared in part (a) of this Example by mixing in PBS at room temperature. Proportions are arrived at by monitoring aggregation induced by liposome under a microscope and increasing liposome concentration until aggregates begin to dissolve. The resultant bridging liposome complex bound to label is washed.

(c) Preparation of Support-Unknown Complex

The unknown (AFP) is immunosorbed on plastic beads (approximately 1 cm diameter) coated with mouse monoclonal antiAFP antibodies (MaAFP). The coated beads, along with human serum controls, are obtained commercially (Hybritech Incorporated, San Diego, Calif.; TANDEM-E AFP Assay). The immunosorption is carried out by treatment of ¼" diameter bead with APF-containing serum in accordance with the procedures described in the literature distributed in conjunction with sales of TANDEM-E AFP. The beads are washed after preparation of the AFP complex.

(d) Preparation of Sandwich

The bridging liposome complex bound to ice nucleating agent prepared in part (b) of this Example is combined with the complex of coated beads bound to unknown prepared in part (c) of this Example. Binding is at room temperature. Nucleus concentration is ca. $10^6$/ml at −10° C. The result is a sandwich which may be viewed as follows:

Macrobead::MaAFP→AFP→(RaAFP::Liposome::-RaINA←s*)

(e) Ice Nucleation Assay

The bead containing the sandwich is washed. Ice nucleating agents are released from the sandwich by treatment of the bead with DTT which reduces the disulfide covalent linkage system and results in the release of nuclei. This is carried out in 2 mM DTT, 20 mM Tris at pH 8, room temperature for 30 minutes. The supernatant from the release steps is diluted 1/10 in Ina (−) buffer and assayed.

The released ice nucleating agents are assayed with the droplet freezing assay in accordance with the Vali procedure (see description of same above).

The concentration of ice nuclei in the sandwich is a direct measure of AFP present in the unknown sample, as compared to standard controls.

EXAMPLE 5

Noncompetitive Sandwich Assay for AFP Using Bridging Antibody

Alpha-fetoprotein (AFP) is assayed in a noncompetitive sandwich assay using soluble bacterial ice nucleating agents bound to the unknown by a bridging antibody as described below.

(a) Bridging Antibody

Goat anti-rabbit immunoglobulin (GaRIG), which has specific affinity for rabbit antibodies of the IgG class (including RaAFP and RaINA) is obtained commercially (Sigma R-3128, IgG fraction).

(b) Preparation of Support-Unknown Complex

This is carried out as in part (c) of Example 4.

(c) Preparation of Sandwich

The support-unknown complex of part (b) of this Example is washed and then combined with the RaAFP. The RaAFP is commercially obtained (CalBiochem). Combining is at 1:200 dilution (based on serum) of RaAFP in buffer G (PBS, 1% w/v BSA, 1:100 Goat Normal Serum, 0.01% thimerosal - Vector Laboratories) at 37° C. for two hours. After washing, the intermediate product (support-unknown bound to RaAFP) is combined with a complex of soluble ice nuclei and RaINA. The ice nuclei are produced in accordance with the procedures of Example 1. The RaINA is obtained as in Example 3. The complex is prepared by reacting RaINA serum (1:2 dilution in PBS, 1% BSA, 0.01% thimerosal) with 1:20 m*, room temperature for 3 hours, and then ultracentrifuging and resuspending in Ina (−) buffer with 0.01% thimerosal at ½ of reaction volume. Subsequently, the mixture of support-unknown bound to RaAFP and complex of label-RaINA is combined with GaRIG from part (a) of this Example. A final wash is performed to remove unbound nuclei from the resultant sandwich, which may be viewed as follows:

Macrobead::MaAFP→AFP→RaAFP→GaRIG←(-RaINA←m*)

(d) Ice Nucleation Assay

The bead is incubated in papain (100 μg/ml), EDTA (2 mM), 2-mercaptoethanol (10 mM) to bring about release of ice nuclei based upon proteolytic cleavage. Incubation is in Ina (−) buffer for 30 minutes to 3 hours followed by dilution 1/10 in Ina (−) buffer.

Assay for ice nuclei, a direct measure of unknown, is carried out with the droplet freezing assay in accordance with the Vali procedure (see description of same above).

What is claimed is:

1. In a method for carrying out immunoassays involving immunological reactions of immunochemical counterparts wherein one of said immunochemical counterparts is linked to a label and wherein the immunoassay determination is related to measurement for the presence of label, the improvement which comprises using a biological ice nucleating agent as the label.

2. The method of claim 1 wherein the biological ice nucleating agent is a bacterial ice nucleating agent.

3. The method of claim 2 wherein the bacterial ice nucleating agent is derived from Pseudomonas or transformed $E.$ $coli.$ 4. The method of claim 1 wherein the improvement further comprises use of a fluorescence freezing assay to measure the presence of the label.

5. In a non-competitive immunoassay to determine the presence of a ligand in a fluid sample comprising (a) combining a fluid sample containing a ligand to be determined with a first receptor specific to the ligand and a conjugate comprising a second receptor specific to the ligand and a label, said label being coupled to said second receptor, and (b) determining the amount of label bound to ligand as a measure of ligand present in the sample, the improvement comprising using a biological ice nucleating agent as the label.

6. The immunoassay of claim 5 wherein the biological ice nucleating agent is a bacterial ice nucleating agent.

7. The immunoassay of claim 6 wherein the bacterial ice nucleating agent is derived from Pseudomonas or transformed $E.$ $coli.$ 8. The immunoassay of claim 5 wherein the improvement further comprises use of a fluorescence freezing assay to measure the presence of the label.

9. In a competitive immunoassay to determine the presence of a ligand in a fluid sample comprising (a) combining a fluid sample containing a ligand to be determined with a receptor specific to the ligand and with a conjugate comprising a second ligand to which the receptor is specific and a label coupled to said second ligand, and (b) determining the amount of receptor bound to the conjugate as a measure of ligand present in the sample, the improvement comprising using a biological ice nucleating agent as the label.

10. The immunoassay of claim 9 wherein the biological ice nucleating agent is a bacterial ice nucleating agent.

11. The immunoassay of claim 10 wherein the bacterial ice nucleating agent is derived from Pseudomonas or transformed $E.$ $coli.$ 12. The immunoassay of claim 9 wherein the improvement further comprises use of a fluorescence freezing assay to measure the presence of the label.

13. A noncompetitive immunoassay method to determine the presence of a ligand in a fluid sample comprising the steps of (a) combining a fluid sample containing a ligand to be quantitated with
  (i) a first receptor specific for the ligand to be quantitated, and
  (ii) a conjugate comprising a second receptor specific for the ligand, and a biological ice nucleating agent coupled to said second receptor; and (b) determining the amount of ice nucleating agent bound to the ligand as a measure of the presence of a ligand in the fluid sample.

14. The immunoassay of claim 13 wherein the biological ice nucleating agent is a bacterial ice nucleating agent.

15. The immunoassay of claim 14 wherein the bacterial ice nucleating agent is derived from Pseudomonas or transformed $E.$ $coli.$ 16. The immunoassay of claim 13 wherein said determining of the amount of ice nucleating agent comprises use of a fluorescence freezing assay.

17. A competitive immunoassay method to determine the presence of a ligand in fluid sample comprising the steps of (a) mixing a fluid sample with
  (i) a receptor specific for the ligand to be determined, and
  (ii) a conjugate comprising a biological ice nucleating agent and a second ligand specific for said receptor, said second ligand coupled to said biological ice nucleating agent; and (b) determining the amount of ice nucleating agent bound to the receptor as a measure of the presence of ligand in the sample.

18. The immunoassay of claim 17 wherein the biological ice nucleating agent is a bacterial ice nucleating agent.

19. The immunoassay of claim 18 wherein the bacterial ice nucleating agent is derived from Pseudomonas or transformed *E. coli.*

20. The immunoassay of claim 17 wherein said determining of the amount of ice nucleating agent comprises use of a fluorescence freezing assay.

21. A reagent for use in an immunoassay to determine the presence of a ligand in a fluid sample, said reagent selected from the group consisting of
    (a) the ligand coupled to a biological ice nucleating agent, and
    (b) a receptor specific to the ligand said receptor coupled to a biological ice nucleating agent.

22. The reagent of claim 21 wherein the biological ice nucleating agent is a bacterial ice nucleating agent.

23. The reagent of claim 22 wherein the bacterial ice nucleating agent is derived from Pseudomonas or transformed *E. coli.*

24. A reagent for use in a noncompetitive immunoassay to determine the presence of a ligand in a fluid sample, said reagent comprising a receptor specific to the ligand and a biological ice nucleating agent coupled to said receptor.

25. The reagent of claim 24 wherein the biological ice nucleating agent is a bacterial ice nucleating agent.

26. The reagent of claim 25 wherein the bacterial ice nucleating agent is derived from Pseudomonas or transformed *E. coli.*

27. A reagent for use in a competitive immunoassay to determine the presence of a ligand in a fluid sample based upon reaction of the reagent with a receptor specific to the ligand, said reagent comprising a biological ice nucleating agent coupled to a ligand immunologically equivalent to the ligand to be determined.

28. The reagent of claim 27 wherein the biological ice nucleating agent is a bacterial ice nucleating agent.

29. The reagent of claim 28 wherein the bacterial ice nucleating agent is derived from Pseudomonas or transformed *E. coli.*

30. A kit for use in a noncompetitive immunoassay to determine the presence of a ligand in a fluid sample, comprising a plurality of containers, one of which contains a first receptor bound to an insolubilized support and specific to the ligand and a second of which contains a conjugate comprising a second receptor specific to the ligand, said second receptor coupled to a biological ice nucleating agent.

31. The kit of claim 30 wherein the biological ice nucleating agent is a bacterial ice nucleating agent.

32. The kit of claim 31 wherein the bacterial ice nucleating agent is derived from Pseudomonas or transformed *E. coli.*

33. A kit for use in a competitive immunoassay to determine the presence of a ligand in a fluid sample, comprising a plurality of containers, one of which contains a receptor bound to an insolubilized support and specific to the ligand and a second of which contains a conjugate comprising a biological ice nucleating agent coupled to a ligand immunologically equivalent to the ligand.

34. The kit of claim 33 wherein the biological ice nucleating agent is a bacterial ice nucleating agent.

35. The kit of claim 34 wherein the bacterial ice nucleating agent is derived from Pseudomonas or transformed *E. coli.*

* * * * *